United States Patent [19]
Smart et al.

[11] Patent Number: 5,286,357
[45] Date of Patent: Feb. 15, 1994

[54] CORROSION SENSORS

[75] Inventors: John D. Smart, Cheshire; William M. Cox, Manchester, both of England

[73] Assignees: British Aerospace Public Limited Company, Farnborough; Capcis March Ltd., Manchester, both of England

[21] Appl. No.: 924,830

[22] Filed: Aug. 4, 1992

[51] Int. Cl.⁵ .................... G01N 27/26; G01N 27/416
[52] U.S. Cl. .............................. 204/153.11; 204/404; 324/71.2; 324/425; 324/448; 324/700
[58] Field of Search .......................... 204/153.11, 404; 324/71.2, 425, 448, 700

[56] References Cited
U.S. PATENT DOCUMENTS 4,780,664 10/1988 Ansuini et al. ..................... 324/700
5,139,627 8/1992 Eden et al. ..................... 204/153.11

*Primary Examiner*—Aaron Weisstuch

[57] ABSTRACT

A corrosion sensor (1), apparatus for detecting corrosion of a surface incorporating the sensor, a structural assembly (1,21) incorporating the sensor and method for detecting corrosion of a surface employing the sensor are provided. The sensor comprises a thin flexible non-conducting substrate (18) for attachment to a surface subject to corrosive influence and an array of at least two thin flexible metallic electrodes (2,3,4) carried on the substrate wherein the electrodes are disposed closely adjacent one another so as to permit the generation of electric current by electrochemical action therebetween upon corrosion of the electrodes.

The apparatus comprises one or more of the corrosion sensors (1) each being attachable to the surface so as to be exposed to the same corrosion conditions as the surface and means (6, 8, 10, 12, 14, 16) for measuring corrosion-induced electrochemical activity between the electrodes to provide an output indicative of the corrosion and the method provides a method of use of the apparatus described.

13 Claims, 1 Drawing Sheet

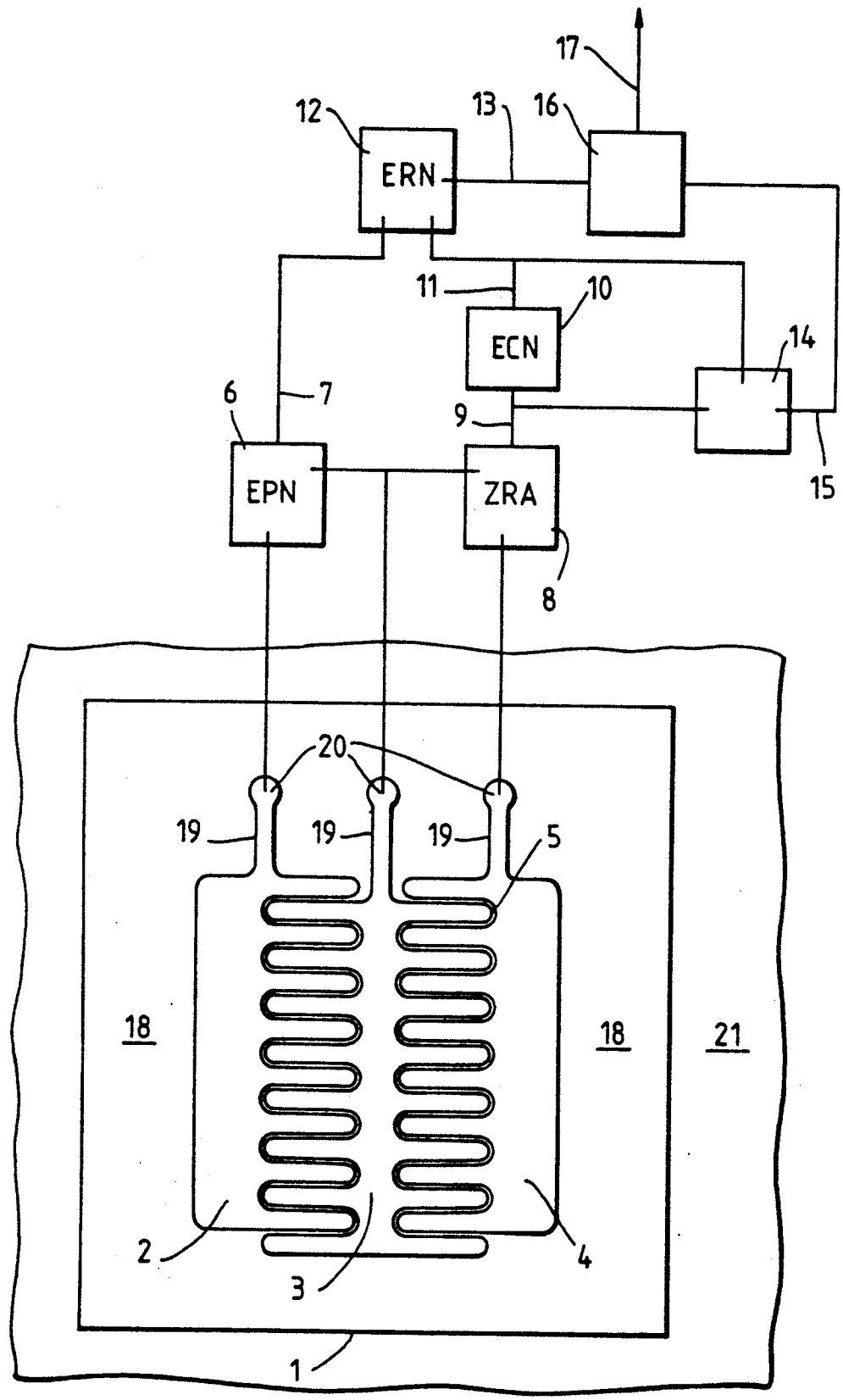

CORROSION SENSORS

BACKGROUND TO THE INVENTION

This invention relates to corrosion sensors for surface corrosion monitoring, coating degradation, and corrosion surveillance applications.

DESCRIPTION OF THE PRIOR ART

It is known that corrosion is an electrochemical phenomenon and that measurements of electrochemical parameters associated with corrosion processes may be used to estimate the rate and the type of corrosion attack. A method and apparatus for assessing a type of corrosion attacking a particular metallic material using electrochemical measurement techniques have previously been detailed in patent PCT/GB87/00310.

The apparatus described in patent PCT/GB87/00310 includes an array of three finger electrodes fabricated from the same material as the metallic surface for which it is desired to measure corrosion and exposed to the same conditions as that surface by being immersed in a tank of corrosive liquid. Achieving a good correlation in the laboratory between the degree and type of corrosion attack on the electrodes and on the metallic surface in use depends on achieving very similar corrosion conditions for both.

This correlation may be readily achievable by apparatus such as that described above for corrosion conditions existing, for example, in pipes which are normally filled by a liquid. However, for corrosion attack on an exposed surface subject only to condensation from a condensing environment such as corrosion occurring on an external aircraft wing or fuselage panel, it can be difficult if not impossible to accurately reproduce the "in use" corrosive conditions.

A further complication is that surfaces of structures subject to corrosion may often be covered with a protective layer, for example paint, and once again the reproduction of such corrosive conditions in a precise manner is extremely difficult.

A third area of variability which is difficult to reproduce in the laboratory is that of stress applied to the structure subject to corrosion. Applied stress, whether variable or fixed in character can effect the breakdown of protective treatments to the surface of the structure concerned, the initiation of any corrosion and the rate of corrosion attack on that surface. Even if possible to reproduce in the laboratory a fixed applied stress, to accurately reproduce the type of variable stress which is encountered by, for example, an aircraft wing panel, is very difficult if not impossible.

SUMMARY OF THE INVENTION

It is the object of the present invention to provide an improved corrosion and degradation sensor to be used in an apparatus and method for detecting localised corrosion of conducting surfaces.

According to one aspect of the present invention there is provided a corrosion sensor comprising a thin flexible non-conducting substrate for attachment to a surface subject to corrosive influence and an array of at least two thin flexible metallic electrodes carried on the substrate, wherein the electrodes co-extend closely adjacent one another so as to permit the spontaneous generation of electrical signals by electrochemical action between the electrodes upon their corrosion.

The invention therefore provides a corrosion sensor which can be attached to a metallic or non-metallic surface for which the corrosion is to be measured and which substantially integrates with its environment so as to allow accurate estimation of corrosion encountered by the surrounding surface.

Each pair of closely adjacent electrodes may be formed in an interleaving pattern one with the other. Such interleaving may take the form of finger portions of each electrode interleaving with finger portions of the other. Such interleaving increases the possible length of co-extension of the electrodes for a given area of surface covered by the sensor.

According to a second aspect of the present invention there is provided apparatus for detecting corrosion of a surface comprising one or more corrosion sensors according to the first aspect of the invention, each of said sensors being attachable to said surface so as to be exposed to the same corrosion conditions as the surface, and means for measuring corrosion-induced electrochemical activity between the electrodes to provide an output indicative of the corrosion.

The corrosion sensor comprised in the apparatus may include three electrodes and the means for measuring corrosion-induced electrochemical activity may comprise means for measuring electrochemical coupling current between one pair of the electrodes and means for measuring electrochemical noise between the same pair or a second pair of the electrodes, and means for comparing the coupling current with the electrochemical current noise to provide an output indicative of the degree to which corrosion is localised.

The apparatus may include means for monitoring electrochemical potential noise between a further pair of electrodes and means for comparing the electrochemical potential noise with the electrochemical current noise to indicate overall rate of corrosion.

The apparatus may also include means to compare the overall rate of corrosion with the degree of localisation of corrosion to give an indication of rate of localised corrosion.

According to a third aspect of the present invention there is provided a method of detecting corrosion of a surface, comprising the steps of attaching a corrosion sensor according to the first aspect of the invention to the surface, subjecting the sensor and surface to a corrosive influence, and measuring corrosion-induced electrochemical activity between the electrodes.

The method may include the steps of measuring the electrochemical coupling current between any pair of electrodes of the array, measuring electrochemical current noise between a second pair of electrodes and comparing the electrochemical coupling current with the electrochemical current noise to provide an output indicative of the degree to which the corrosion is localised.

According to a fourth aspect of the invention there is provided a structural assembly comprising at least one panel member and at least one corrosion sensor according to the first aspect of the invention attached to the at least one panel member, said at least one panel member and at least one corrosion sensor being exposable simultaneously to a common corrosive influence.

BRIEF DESCRIPTION OF THE DRAWINGS

One embodiment of the invention will now be described, by way of example only, and with reference to the accompanying drawing schematically illustrating one embodiment of the sensor mounted on a panel surface and connected to electronic measuring apparatus.

DESCRIPTION OF PREFERRED EMBODIMENT

A preferred sensor arrangement 1 has a configuration of three interleaved electrodes, 2, 3, and 4 having a gap 5, typically 0.25 mm., therebetween mounted upon a thin, non-conductive, substantially flexible substrate material 18. The sensor 1 is mounted by adhesive to the surface of a panel 21, the corrosive activity upon which is to be estimated by the use of the sensor 1. The substrate material 18 is of cast or laminate polyimide and is 150-200 micrometers thick. Use of epoxy resins for the substrate is also possible. The overall size of the sensor is between 25 and 50 mm square. Each of the electrodes includes an extension 19 terminating in a terminal 20.

Electrodes 2 and 3 are connected to an electrochemical potential noise monitoring apparatus 6 which provides on output 7 an output signal representative of the RMS or standard deviation of the potential noise. The electrochemical noise may be monitored as shown by a circuit connected between the coupled electrodes 3 and 4 and a third electrode 2 of the array. A zero resistance ammeter 8 is connected across electrodes 3 and 4 and produces on output 9 an output signal corresponding to the DC coupling current.

The output 9 is connected to an electrochemical current noise apparatus 10 which provides on output 11 an output signal corresponding to the RMS or standard deviation of the current noise. The outputs 7 and 11 are applied to a circuit 12 for comparing the electrochemical potential noise and the electrochemical current noise. The circuit 12 provides on output 13 an output signal which is the resistive or impedance noise and is equal to the ratio of the electrochemical potential noise to the electrochemical current noise. The output 13 is effectively indicative of the overall rate of corrosion.

The illustrated structure provides effectively four outputs, each of which varies in a manner which is indicative of the rate and/or nature of the corrosion attack to which the electrode array is exposed. A comparison made between the signals on outputs 9 and 11 indicates the nature of the corrosion attack. Accordingly, a comparator circuit 14 is connected to outputs 9 and 11 and provides on output 15 an output signal which is representative of the ratio between the electrochemical noise and the DC coupling current.

Output 15 is indicative of the degree or otherwise of localised behaviour during corrosion attack. That is, a low value of the ratio is indicative of general corrosion, while a high value is indicative of localised corrosion.

A further circuit 16 is provided which compares the output 13 (overall corrosion rate) with the output 15 (degree to which corrosion is localised) and produces an output 17 which is indicative of the rate of localised corrosion. Thus use of the apparatus of the present invention makes it possible accurately to determine both the nature and rate of a particular corrosion process.

The electrode material can be of any pure metal, alloy or metal-based composite material which can be mechanically prepared or applied by deposition methods such as plating, adhesion, laser methods, or vapour-deposition techniques such as evaporation, ion-plating, reactive ion-plating and sputtering. Typical materials are aluminium, magnesium, lithium, zinc, titanium, and alloys of these metals. The thickness of these electrodes can be varied depending on the application but would typically be 5-25 $\mu$m thick.

The overall size of the sensor can be varied depending on requirements but might typically be 25-50 mm square. In practice, the sensors are located on or adhesively bonded to structures to which a corrosion-resisting protective coating may be applied subsequently as appropriate. They can be used for detecting the breakdown or damage of passive films, organic films, or protective coatings applied to metallic or non-metallic structures and for monitoring and/or estimating the severity and type of corrosion representative of damage sustained by the surrounding structure. Sensors of this type can also be used for providing a rapid indication of cracking of a structure due to a corrosion enhanced or assisted mechanism. The sensors may also be designed to monitor the corrosivity of the surrounding environment.

The sensors are monitored as described above to detect general breakdown or localised damage to the protective coating and to monitor electrochemical activity generated by the sensor films to detect the onset of corrosion or to provide an estimate of the rate, severity, and type of corrosion which could be expected in the surrounding structure.

Sensors which have not been coated can be monitored to give a rapid indication of the type of environment experienced in those particular areas of the structure in which the sensors are located. Cracking of the structure in the areas to which the sensors are bonded, for example due to stress corrosion cracking or corrosion fatigue, may also be determined by the detection of electrochemical signals generated by the sensor films and/or between the structure (so long as it contains conducting fibres therein) and one or more of the individual metallic films on the sensors.

Such signals may be generated upon the breakdown of the non-conductive substrate of the sensor to allow electrochemical activity to take place between one or more of the electrodes and the conductive material of the surface to which the sensor is applied. Alternatively, the sensor may be applied to the conducting surface so that the electrodes face the surface but are spaced therefrom by a small distance of the order of 0.1 to 0.5 mm. The incursion of a corrosive solution between sensor and surface will then precipitate electrochemical activity between the surface and at least one electrode of the sensor. It is of course necessary to provide an electrical connection between the instrumentation and the conductive surface as well as the sensor for this purpose.

The principal advantages of the metal corrosion sensors of the invention are:

1) The sensors are thin, relatively flexible, and can be attached to a structure such that they follow the contours thereof and protrude only slightly above the surface of the structure. This results in only a minimal disturbance of the gas or liquid flow around the sensors and allows any condensation or contamination on the surface or the structure to also affect the sensor electrodes.

2) The sensors can be physically attached (e.g. by adhesive bonding) to a structure so that any strain applied to that structure can influence the corrosion or degradation performance of the sensors and any protective treatment applied over the sensors. It is known that in aircraft, highly strained coated or uncoated areas of the structure may display a significantly different corrosion performance compared with unstrained areas.

3) The low thermal capacity of the sensors does not affect heat transfer to the substrate and/or surface to which it is attached, allowing accurate monitoring of condensation-induced corrosion.

4) The sensors may be attached to the structure prior to the application of a protective treatment (e.g. paint) to the structure. The protective treatment may then be applied over the structure and the sensor in one operation.

5) The size, composition, structure, thickness, and geometry of the metallic films and the backing material can be varied to produce a combination reflecting the materials and design of the structure to which the sensors will be attached.

6) A large number of the sensors can be attached to a structure in which weight is important e.g. aircraft.

7) The sensors are relatively cheap to manufacture.

8) The apparatus using the sensors is more sensitive to the onset of degradation than are apparatuses using conventional electrical resistance type sensors and can be used to predict the onset of attack. They may also be used to provide an estimate of the rate and type of damage.

9) The sensors are particularly sensitive for the detection of localised corrosion activity such as pitting corrosion, crevice corrosion, stress corrosion, cracking corrosion fatigue, under deposit corrosion, coating or composite structure degradation, and under-coating corrosion.

In a typical sensor design as shown in the attached drawing illustrating an interleaved three-electrode configuration, the high degree of interleaving shown would result in a high level of electrochemical signals produced by the sensor as the length of electrode co-extension per unit area of the sensor is increased compared with straight electrodes with straight lines of co-extension.

The electrode geometry can be varied according to the application and could be of a simple rectangular or a more complex interleaved type. The gap between the electrodes, while being typically 0.25 mm, may be larger or smaller as desired. The gap between the electrodes should be sufficiently small for the corrosive environment to form an electrochemical "bridge" with a reduced solution resistivity between the electrodes and so can be varied according to the severity and type of corrosion which will be experienced by the sensor.

The substrate material can be varied; for example polystyrene could be used.

We claim:

1. Apparatus for detecting corrosion of a surface, comprising
   at least one corrosion sensor comprising a thin flexible non-conducting substrate and an array of at least two thin flexible metallic electrodes carried on said substrate, wherein said electrodes co-extend closely adjacent one another so as to permit spontaneous generation of electrical signals by electrochemical action between said electrodes upon their corrosion, said at least one sensor being attachable to said surface so as to be exposed to the same corrosive conditions as said surface, and
   means for measuring, without the application of any electrical potential to said at least one corrosion sensor, corrosion-induced electrochemical activity between said electrodes to provide an output indicative of the corrosion.

2. Apparatus as in claim 1 wherein said electrodes co-extend closely adjacent one another with a gap therebetween of substantially 0.25 mm.

3. Apparatus as in claim 1 wherein said means for measuring corrosion-induced electrochemical activity between said electrodes includes means for measuring electrochemical coupling current between a first pair of said electrodes, means for measuring electrochemical noise between a second pair of said electrodes, and means to compare said coupling current with said current noise to provide an output indicative of the degree to which corrosion is localized.

4. Apparatus as in claim 3 including means for monitoring electrochemical potential noise between a further pair of said electrodes and means for comparing said electrochemical potential noise with said electrochemical current noise to indicate the overall rate of corrosion.

5. Apparatus as in claim 4 including means to compare said overall rate of corrosion with said degree of localization of corrosion to give an indication of rate of localized corrosion.

6. A structural assembly comprising at least one panel member and at least one corrosion sensor according to claim 1 attached to said at least one panel member, said at least one panel member and at least one corrosion sensor being exposable simultaneously to a common corrosive influence.

7. A method of detecting corrosion of a surface, comprising the steps of
   attaching to the surface a corrosion sensor comprising a thin, flexible, non-conducting substrate and an array of at least two thin, flexible, metallic electrodes carried on said substrate, wherein said electrodes co-extend closely adjacent one another so as to permit spontaneous generation of electrical signals by electrochemical action between said electrodes upon their corrosion,
   subjecting said sensor and surface to a corrosive influence, and
   measuring, without the application of any electrical potential to said corrosion sensor, corrosion-induced electrochemical activity between said electrodes.

8. A method of detecting breakdown of a protective coating applied to a surface subject to corrosive influence, including the steps of
   attaching to said surface at least one corrosion sensor comprising a thin, flexible, non-conducting substrate and an array of at least two thin, flexible, metallic electrodes carried on said substrate, wherein said electrodes co-extend closely adjacent one another so as to permit spontaneous generation of electrical signals by electrochemical action between said electrodes upon their corrosion,
   applying said protective coating to cover both said surface and said at least one corrosion sensor, and
   measuring, without the application of any electrical potential to said corrosion sensor electrodes, corrosion induced electrochemical activity between said electrodes.

9. A method of detecting cracking in a surface of a structure by corrosion measurement, including the steps of
   attaching to said surface in a position subject to both the possibility of cracking and to corrosive influence a corrosion sensor comprising a thin, flexible, non-conducting substrate and an array of at least two thin, flexible, metallic electrodes carried on said substrate, wherein said electrodes co-extend closely adjacent one another so as to permit spontaneous generation of electrical signals by electrochemical action between said electrodes upon their corrosion in such a manner that said cracking will break down the insulation of the non-conducting substrate and permit corrosion induced electrochemical activity to take place between said structure and at least one of said electrodes of said corrosion sensor, and measuring, without the application of any external electrical potential to said substrate of said corrosion sensor by measuring apparatus, corrosion induced electrochemical activity between said structure and at least one of said electrodes.

10. A method of measuring mechanical strain of a structure by comparative corrosion measurement, including the steps of attaching to a surface of said structure subject to both mechanical strain and corrosive influence a first corrosion sensor comprising a thin, flexible, non-conducting substrate and an array of at least two thin, flexible, metallic electrodes carried on said substrate, wherein said electrodes co-extend closely adjacent one another so as to permit spontaneous generation of electrical signals by electrochemical action between said electrodes upon their corrosion, whereby said first corrosion sensor will be subject to substantially the same mechanical strain and corrosive influence as said surface, positioning a second said corrosion sensor to be subject to substantially the same corrosive influence as said first corrosion sensor but not to be subject to said mechanical strain, measuring, without applying any external electrical potential to either of said corrosion sensors, corrosion induced electrochemical activity between said electrodes of each said corrosion sensor, and comparing the values measured to give an indication of mechanical strain of the structure.

11. A structural assembly comprising at least one panel member, and apparatus for detecting corrosion of a surface, including at least one corrosion sensor comprising a thin, flexible, non-conducting substrate for attachment to a surface subject to corrosive influence and an array of at least two thin, flexible, metallic electrodes carried on said substrate, wherein said electrodes co-extend closely adjacent one another so as to permit spontaneous generation of electrical signals by electrochemical action between said electrodes upon their corrosion, said at least one sensor being attachable to said surface so as to be exposed to the same corrosive conditions as said surface, and means for measuring, without the application of any electrical potential to said at least one corrosion sensor, corrosion-induced electrochemical activity between said electrodes to provide an output indicative of the corrosion, said at least one corrosion sensor being attached to said at least one panel member so as to be exposed simultaneously to a common corrosive influence.

12. A structural assembly as in claim 11 wherein said at least one panel member and said at least one corrosion sensor are covered by a common protective coating.

13. A structural assembly as in claim 11 wherein said apparatus for detecting corrosion is electrically connected to said at least one panel member and to said at least one corrosion sensor whereby to measure corrosion induced electrochemical activity between said panel member and at least one electrode of a said corrosion sensor upon insulation breakdown of said non-conductive substrate.

* * * * *